US00PP18143P2

(12) United States Plant Patent
Olesen

(10) Patent No.: US PP18,143 P2
(45) Date of Patent: Oct. 23, 2007

(54) MINIATURE ROSE PLANT NAMED 'POULPAR043'

(50) Latin Name: ***Rosa* hybrid**
Varietal Denomination: Poulpar043

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/442,557

(22) Filed: May 26, 2006

(51) Int. Cl.
*A01H 5/00* (2006.01)

(52) U.S. Cl. ..... Plt./122

(58) Field of Classification Search ..... Plt./122
See application file for complete search history.

*Primary Examiner*—Kent Bell
*Assistant Examiner*—Annette H Para

(57) ABSTRACT

A new miniature rose plant that has abundant, red flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar043'.

SUMMARY OF THE INVENTION

The present discovery constitutes a new and distinct variety of miniature rose plant which was discovered in a cultivated area. The new rose variety resulted from a naturally occurring mutation of unknown causation on a branch of 'Poulpar029', U.S. Plant Pat. No. 16,148. The resulting mutation was selected and evaluations were conducted on the resulting rose plants in a controlled environment.

The rose plant of the present discovery has a unique combination of characteristics which are outstanding in the new variety and which distinguish it from the original rose 'Poulpar029' as well as all other varieties which we are aware of. For example, 'Poulpar029' has a general flower color of Red Group 53A. 'Poulpar043' has a general flower color of Red Group 40A. 'Poulpar043' also has flowers which are slightly larger than 'Poulpar029.'

The criteria used to evaluate the claimed plant were selected in order to introduce a distinct variety for garden use with unique qualities, such as:

1. Uniform and abundant red flowers;
2. Vigorous, but very compact growth when propagated both as a budded rose and on its own roots;
3. Exceptional disease resistance; and
4. Long lasting flowers.

This combination of qualities is not present in previously available commercial cultivars of this type, known to the inventor, and distinguish 'Poulpar043' from all other varieties of which we are aware.

Asexual reproduction of 'Poulpar043' by vegetative cuttings was first done by Mogens N. Olesen in Fredensborg, Denmark, in July of 2001. This initial and other subsequent propagations have demonstrated that the characteristics of 'Poulpar043' are stable and reproduced true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar043'. Specifically illustrated in the drawing are the following:

FIG. 1.1 Open flower;

FIG. 1.2; Side view of a flower bud closed, partially open, and open;

FIG. 1.3; Flower petals, detached;

FIG. 1.4; Sepals, receptacle, and pedicel;

FIG. 1.5; Bare stem exhibiting prickles;

FIG. 1.6; Leaves.

DETAILED DESCRIPTION OF THE VARIETY

The following is a description of 'Poulpar043', as observed in its growth in a glasshouse in Fredensborg, Denmark. Observed plants are 4 months of age and were cultivated in 10.5 cm pots. Color references are made using The Royal Horticultural Society (London, England) Colour Chart, 2001, except where common terms of color are used.

FLOWER AND FLOWER BUD

Blooming habit: Continuous.
Flower bud:

*Size.*—Upon opening, an average of 20 mm in length from base of receptacle to end of bud. Bud diameter is typically 8 to 10 mm.

*Bud form.*—Pointed ovoid.

*Bud color.*—As sepals unfold, petals are Red Group 40A.

*Sepals.*—Upper Surface: Color: Yellow-Green Group 147A to Green Group 143C. Anthocyanin at sepal apecies the color of Greyed-Orange Group 176A. Surface: Smooth and lightly pubescent. Lower Surface: Color: Yellow-Green Group 144A. Anthocyanin the color of Greyed-Orange Group 176A, located at sepal apecies. Texture: Smooth. Very light pubescence. Sepal Shape: Sepal apex is cirrhose. Base is flat at union with receptacle. Sepal Margin: 2 of the 5 sepals are entire. Medium to weak foliaceous appendages on three of the five sepals. Stipitate glands observed at margins. Size: 20 to 30 mm (l)×5 mm (w). With foliaceous appendages sepals are 10 mm wide.

*Receptacle.*—Surface: Smooth. Shape: Urn-shaped. Size: 5 mm (l)×5 mm (w). Color: Yellow-Green Group 144A.

*Peduncle.*—Surface: Prickles in medium quantity. Length: 40 to 45 mm. Color: Yellow-Green Group 144A. Strength: Upright and strong.

*Borne.*—1 to 3 flower buds per flowering branch.

Flower bloom:

*Fragrance.*—Very light floral scent.

*Duration.*—As a pot plant, flowers typically last up to 21 days.

*Size.*—Flower diameter is normally 40 mm when open. Flower depth is 20 mm on average.

*Form.*—General shape is a rosette flower with many slightly overlapping petals of different sizes, arranged.

*Shape of flower when viewed from the side.*—Upon opening, upper part: Flat. Upon opening, lower part: Flattened Convex. Open flower, upper part: Convex. Open flower, lower part: Flattened Convex.

Petalage: There are normally 25 to 30 petals, 3 of which are petaloids.

Flower color:

*Upon opening petals.*—Outermost and Innermost Petals: Lower Surface: Red Group 40A. Inner Side: Red Group 40A.

*Upon opening, basal petal spots.*—Lower Surface: White Group 155A. Upper Surface: White Group 155A.

*After opening, petals.*—Outermost and Innermost Petals: Lower Surface: Red Group 40A. Upper Surface: Red Group 40A.

*After opening, basal petal spots.*—Outermost and Innermost petals: Lower Surface: White Group 155A. Upper Surface: White Group 155A.

General tonality: On open flower Red Group 40A. No change in the general tonality observed.

Petals:

*Petal reflex.*—Strongly on outer petals. Inner petals reflex only slightly.

*Margin.*—Entire, with a shallow point in the center of the apex.

*Shape.*—Overall shape is deltoid. The petal apex is rounded. The petal bases vary from acute to slightly rounded.

*Size.*—Outer petal: 20 mm (l)×17 mm (w). Inner petal: 15 mm (l)×14 mm (w).

*Texture.*—Smooth.

*Surface gloss.*—Upper petal surfaces are somewhat glossy, while lower petal surfaces are more matte in their finish.

*Thickness.*—Thick.

Petaloids:

*Quantity.*—3 on average.

*Shape.*—Irregular, deltoid.

*Color.*—Red Group 40A on both upper and lower surfaces. The petaloid base is colored White Group 155A at the point of attachment.

*Size.*—Normally 10 mm (l)×6 mm (w).

Reproductive organs:

*Anthers.*—Size: Normally 2 mm long. Color: Yellow Group 12C. Quantity: 50 to 55.

*Filaments.*—Color: Yellow Group 11C with intonations of Red Group 41C. Length: 4 to 5 mm.

*Pollen.*—None observed.

*Pistils.*—Length: Normally 4 mm. Quantity: 30 to 35.

*Stigmas.*—Inferior in location relative to the height of the anthers. Color: Greyed-Yellow Group 162D.

*Styles.*—Color: Greyed-Yellow Group 162D.

*Hips.*—None observed plants cultivated in 10.5 cm pots.

PLANT

Plant growth: Vigorous, very compact, upright and moderately bushy. When grown as a 10.5 cm pot plant, the average height of the plant itself is 18 cm and the average width is 10 cm.

Stems:

*Color.*—Young wood: Yellow-Green Group 146A. Older wood: Yellow-Green Group 146A.

*Internodal distance.*—15 mm.

*Length of stems.*—13 cm.

*Surface texture.*—Young wood: Smooth. Older wood: Smooth.

Prickles:

*Incidence.*—7 to 9 per 10 cm of stem.

*Size.*—Average length: 4 mm.

*Color.*—Mature thorns are Greyed-Red Group 179D. Juvenile thorns are generally Yellow-Green Group 145B.

*Shape.*—Linear.

Plant foliage: There are normally 5 leaflets on leaves in middle of the stem.

*Compound leaf size.*—75 mm (l)×41 mm (w).

*Quantity.*—8 leaves per 10 cm of stem.

*Color.*—Juvenile foliage: Upper Leaf Surface is Yellow-Green Group 144A. Lower Leaf Surface is Yellow-Green Group 147C with anthocyanic pigmentation the color of Greyed-Orange Group 177A to 176B. Anthocyanin: On plants grown under high light conditions, the leaf margins and undersides of developing leaves may exhibit anthocyanic intonations of Greyed-Orange Group 177A to 176B. Mature foliage: Upper Leaf Surface is Green Group 147A. Lower Leaf Surface is Greyed-Green Group 194A.

Plant leaves and leaflets:

*Stipules.*—Size: 15 mm (l)×4 mm (w). Shape: Linear, slightly broad based with outward extending apecies. Extensions are 5 mm in length. Margins: Finely serrated with stipitate glands. Color: Yellow-Green Group 146A.

*Petiole.*—Length: 23 mm. Color: Above: Yellow-Green Group 146B with intonations of Greyed-Orange Group 176A. Underneath: Yellow-Green Group 144B. Small prickles observed. Margins: Stipitate glands observed.

*Rachis.*—Size: 20 mm. Color: Above: Yellow-Green Group 146B with intonations of Greyed-Orange Group 176A. Underneath: Yellow-Green Group 144B. Small prickles normally located mid-way between leaflets. Margins: Stipitate glands observed.

*Leaflet*.—Size: 31 mm (l)×18 mm (w). Edge: Serrated. General Shape: Elliptical. Apex Shape: Acute. Base Shape: Round to acute. Texture: Smooth. Arrangement: Odd pinnate. Venation: Reticulate. Leaf Gloss: Moderately glossy.

Disease resistance: Average resistance to powdery and downy mildew, black spot, and *Botrytis* under normal growing conditions in Fredensborg, Denmark.

It is claimed:

1. A new and distinct variety of rose plant of the miniature class named 'Poulpar043', substantially as illustrated and described herein, due to its abundant, red flowers, vigorous growth, compact habit, suitability for production from softwood cuttings in pots, and durable flowers and foliage that make the variety suitable for distribution in the floral industry.

* * * * *

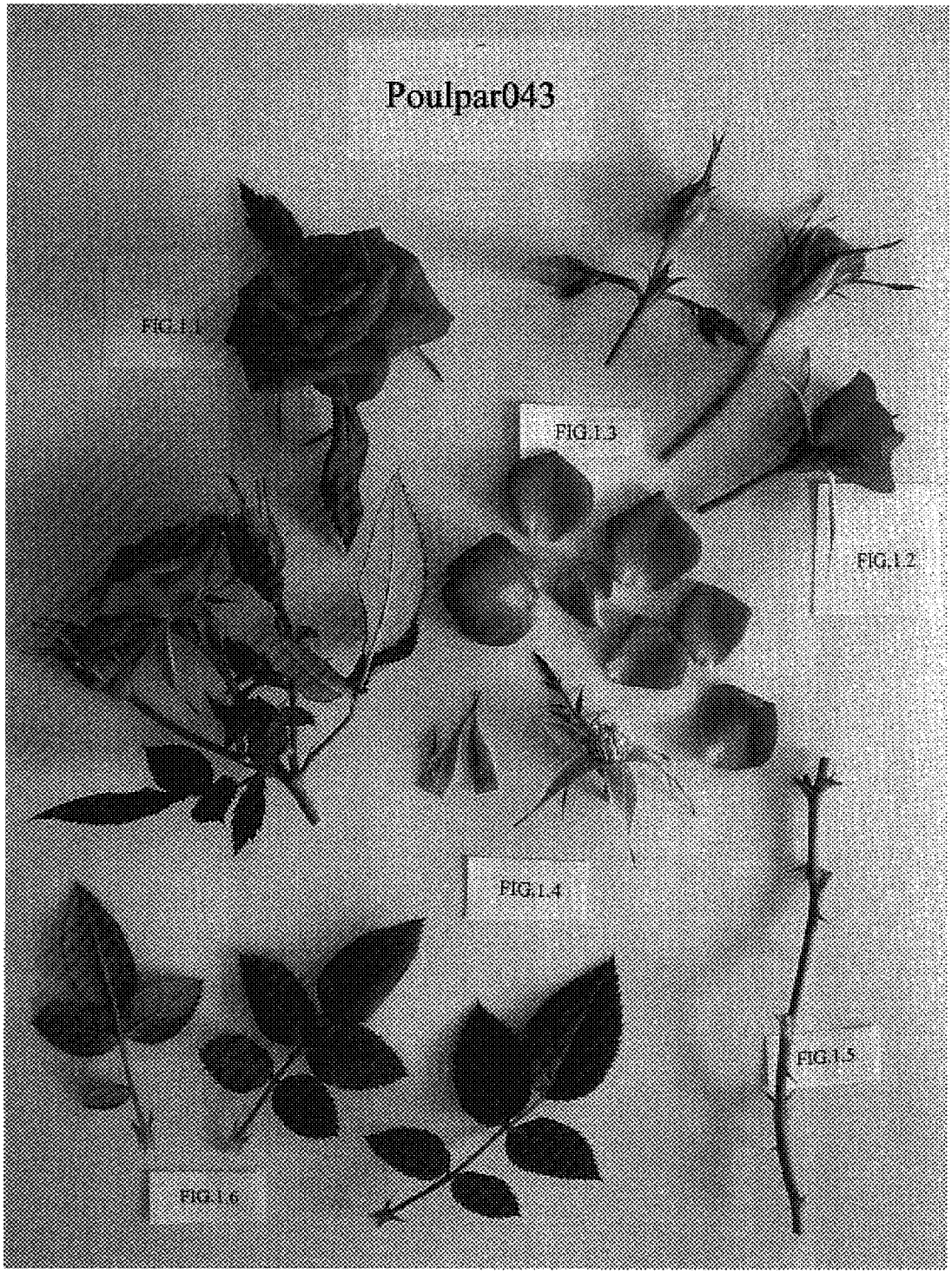
Poulpar043
FIG.1.1
FIG.1.2
FIG.1.3
FIG.1.4
FIG.1.5
FIG.1.6